United States Patent [19]

Sorich et al.

[11] Patent Number: 5,213,573

[45] Date of Patent: May 25, 1993

[54] IV ADMINISTRATION SET INFILTRATION MONITOR

[75] Inventors: Richard A. Sorich, Encinitas; David Burkett, San Diego, both of Calif.

[73] Assignee: IMED Corporation, San Diego, Calif.

[21] Appl. No.: 741,257

[22] Filed: Aug. 5, 1991

[51] Int. Cl.⁵ ............................................. A61M 31/00
[52] U.S. Cl. ..................................... 604/66; 604/62; 604/153; 128/DIG. 12; 128/DIG. 13
[58] Field of Search ............... 604/65, 66, 67, 250, 604/251, 153; 128/DIG. 12, DIG. 13

[56] References Cited

U.S. PATENT DOCUMENTS

| | | | |
|---|---|---|---|
| 4,816,019 | 3/1989 | Kamen | 128/DIG. 13 X |
| 4,846,792 | 7/1989 | Bobo, Jr. et al. | 128/DIG. 13 X |
| 4,979,940 | 12/1990 | Bobo, Jr. et al. | 128/DIG. 13 X |
| 5,087,245 | 2/1992 | Doan | 604/67 |
| 5,096,385 | 3/1992 | Georgi et al. | 604/67 X |

*Primary Examiner*—Randall L. Green
*Assistant Examiner*—Mary Beth O. Jones
*Attorney, Agent, or Firm*—Nydegger & Associates

[57] ABSTRACT

An apparatus for determining whether an IV infusion set has infiltrated the tissue of a patient includes a pump for pumping fluid through the IV set into the patient and a pressure transducer operably engaged with the IV set between the pump and patient. The pressure transducer is electrically connected to a microprocessor, and the microprocessor is electrically connected to the motor of the pump to control the pump to alternately withdraw from and infuse into the patient a predetermined volume of fluid.

This predetermined volume of fluid is withdrawn from the patient by the pump at a preselected withdrawal pressure, while the pump infuses the predetermined volume of fluid into the patient at a preselected infusion pressure. The microprocessor measures both the time period for infusing the predetermined volume of fluid and the time period for withdrawing the predetermined volume of fluid. Based upon these time periods, the microprocessor evaluates whether the IV set has infiltrated the patient's tissue.

15 Claims, 3 Drawing Sheets

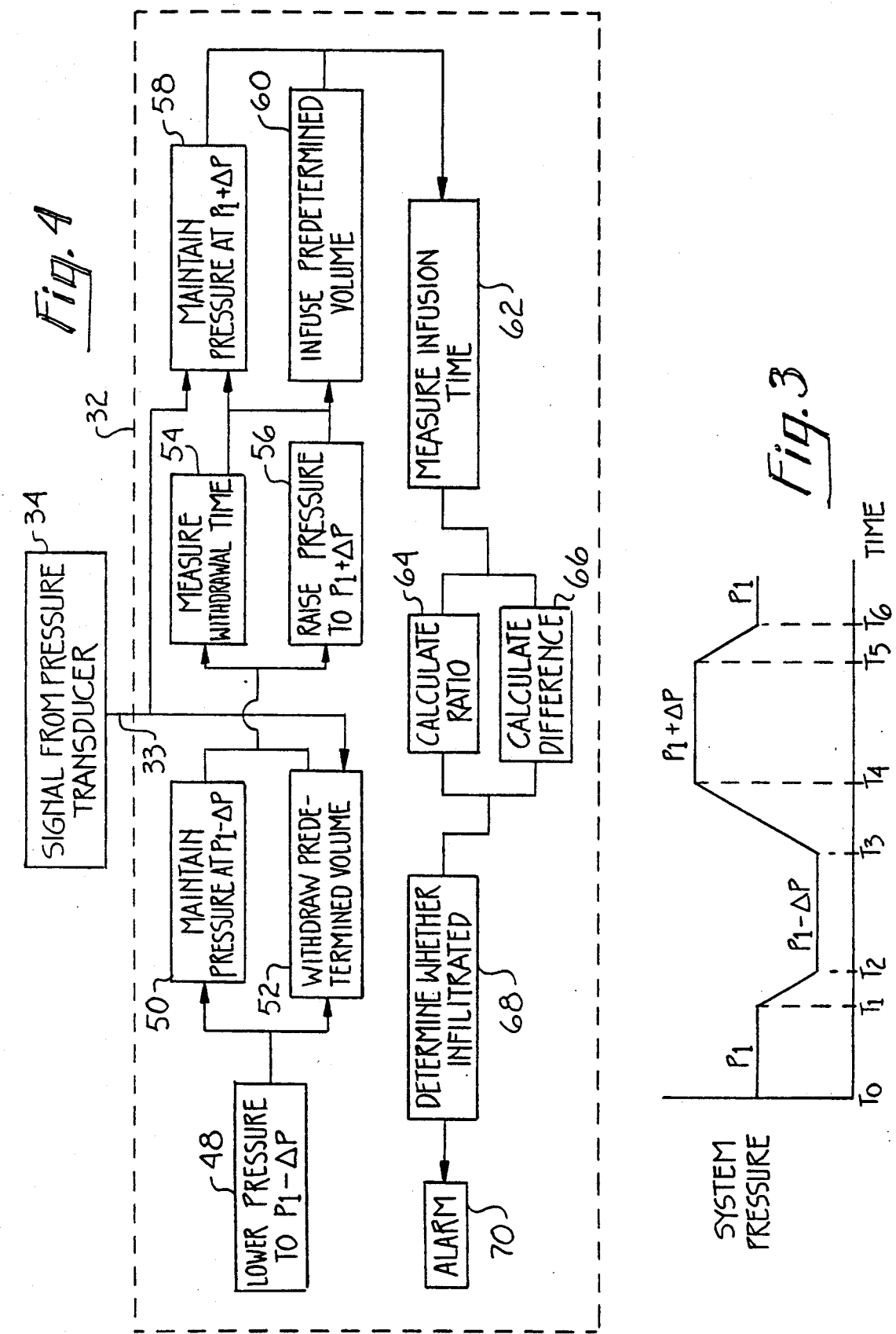

IV ADMINISTRATION SET INFILTRATION MONITOR

FIELD OF THE INVENTION

The present invention relates generally to intravenous (IV) infusion apparatus. More particularly, the present invention relates to methods and apparatus for monitoring the proper operation of an IV infusion procedure. The present invention is particularly, though not exclusively, useful for determining whether an IV administration set has infiltrated a patient's tissue.

BACKGROUND OF THE INVENTION

Intravenous (IV) infusion therapy is a widespread medical technique in which fluid nutrients or fluid medicaments are infused into the bloodstream of a patient through an IV tube as part of treating the patient for a particular malady. More specifically, in infusion therapy, one end of an IV tube is connected to a needle and the needle is inserted through the skin into one of the patient's blood vessels. This establishes a path for fluid communication from the IV tube to the blood vessel. The other end of the IV tube is connected to a source of fluid nutrients or medicaments. The fluid nutrients or medicaments are then pumped through the IV tube or drained by gravity through the IV tube into the patient's bloodstream.

While infusion therapy has proven effective in treating a wide range of maladies, it is not without potential complications. One complication, which is of particular concern, is infiltration of the fluid from the IV set into the patient's tissue. More particularly, it sometimes happens that the medical technician who inserts the needle of the IV tube into the patient may fail to properly insert the needle into a blood vessel and instead the needle is inserted into the tissue which surrounds the blood vessel. This results in infiltration of the IV fluid into the patient's tissue.

Infiltration of IV fluid into a patient's tissue can also occur during the course of fluid infusion to a patient even though the IV set was originally established for proper operation. For example, a needle which was originally properly inserted into a blood vessel may nevertheless inadvertently become separated from the blood vessel. This separation can be caused by a number of factors, e.g., patient motion. Of course, in any case wherein the needle is not in fluid communication with the blood vessel, the fluid to be infused will not be infused into the patient's bloodstream, but instead will be infused into the tissue surrounding the blood vessel. In other words, the infusion needle can be dislocated from the blood vessel and consequently cause the infused fluid to become infiltrated into the patient's tissue. The result, in any event, is an abnormal flow of fluid through the IV administration set.

Infiltration of fluid medicaments or nutrients directly into a patient's tissue is undesirable for several reasons. First, certain fluids cannot be efficiently absorbed by the body when the fluid infiltrates tissue. Thus, infiltration of an IV fluid directly into the tissue surrounding a blood vessel can effectively prevent the patient from receiving the prescribed dosage of nutrients or medicament. Second, infiltration of fluids into body tissue can cause considerable pain to the patient and lead to severe complications which could conceivably require amputation or skin grafts.

It is unfortunately the case that in many circumstances, infiltration of IV liquids into a patient's tissue can go unnoticed by hospital personnel for relatively lengthy periods. This is because it is not feasible for medical establishments to routinely provide personnel who can continuously monitor each and every IV infusion procedure that the medical establishment undertakes. Thus, it is desirable to automatically monitor the conduct of IV infusion procedures to ensure that the infused liquid is indeed being infused into the patient's bloodstream and not into the patient's tissue.

Additionally, it is desirable to monitor IV infusion procedures for infiltration without having to reconfigure the IV administration set each time the monitoring evolution is to be conducted. Stated differently, it is desirable to be able to monitor an IV infusion procedure for infiltration without having to periodically open and shut isolation valves in the IV tube in order to permit monitoring of the infusion process. This is because such valve manipulation can be labor-intensive, if done manually, or require relatively expensive electric valve operators, if the manipulation is to be done automatically.

As recognized by the present invention, it is possible to determine whether an IV set is infiltrated into a patient's tissue by monitoring for abnormal characteristics of the flow through the IV set. The present invention accomplishes this by monitoring fluid flow characteristics in the IV set both during the withdrawal of fluid from a patient and during the infusion of fluid to the patient.

Accordingly, it is an object of the present invention to provide a method and apparatus for determining whether an IV infusion set has become infiltrated in a patient's tissue. It is a further object of the present invention to provide a method and apparatus to automatically monitor the conduct of an infusion therapy procedure without requiring reconfiguration of the IV administration set. Yet another object of the present invention is to provide an apparatus which can alarm to indicate the occurrence of IV set infiltration during infusion therapy and alert medical personnel of the infiltration. Finally, it is an object of the present invention to provide an IV set infiltration monitoring method and apparatus that is easy to use and cost-effective to manufacture.

SUMMARY

A method for determining whether an IV administration set is infiltrated into the tissue of a patient includes the steps of alternately withdrawing fluid from a patient and then infusing fluid to the patient. Selected components of the flow characteristics of the fluid during withdrawal and infusion are measured and evaluated to determine whether the IV administration set is infiltrated into the patient's tissue. An apparatus for determining whether an IV administration set is infiltrated into the tissue of a patient in accordance with the method of the present invention is also disclosed.

More specifically, this apparatus includes a source of fluid, an IV tube which connects the fluid source in fluid communicating with the patient, and a fluid pressure generator (e.g. a peristaltic pump) operably engaged with the IV tube for influencing the flow of fluid through the tube from the source to the patient. Preferably, the pump or fluid pressure generator (hereinafter referred to as pump) is activated by a stepper motor. A pressure transducer is operatively engaged with the IV tube between the patient and the pump to sense fluid pressure in the IV tube. This pressure transducer is electrically connected to a microprocessor and, in turn, the microprocessor is electrically connected to the stepper motor of the pump to control the operation of the pump.

More particularly, during an infiltration check, the microprocessor first controls the stepper motor to operate the pump in a reverse mode to withdraw a predetermined volume of fluid from the patient at a preselected infusion pressure. This particular sequencing, i.e. withdrawal first and then infusion, is done in order to avoid misreadings which might be caused if a volume of fluid is established at the tip of the needle during the infusion step. For the present invention, the predetermined volume of fluid is approximately fifteen microliters (15 μl) and the preselected infusion pressure is equal to a datum pressure minus approximately one half (0.5) pound per square inch (psi). To withdraw the predetermined volume, the microprocessor first correlates the predetermined volume to be infused to a number of discrete operational "steps" of the stepper motor, and then causes the stopper motor to rotate through this correlated number of steps. The pump is consequently activated by the stepper motor to withdraw the predetermined volume of fluid from the patient. The preselected fluid pressure during withdrawal is maintained by the microprocessor, which controls the rotational rate of the stepper motor in accordance with fluid pressure indications from the pressure transducer.

The time period for the withdrawal of this predetermined volume at the preselected infusion pressure is measured by the microprocessor. The microprocessor then causes the stepper motor of the pump to operate in a forward mode for the same number of "steps" which has been correlated to the predetermined volume of fluid. Accordingly, the stepper motor causes the pump to operate in a forward mode to infuse the predetermined volume of fluid into the patient. This fluid withdrawal is conducted at a preselected withdrawal pressure which is equal to the datum pressure plus about one half (0.5) psi. To maintain fluid pressure in the IV tube at the preselected infusion pressure, as indicated by the pressure transducer, the microprocessor controls the rate of rotation of the rotor of the stepper motor in the forward mode.

In accordance with the present invention, the microprocessor determines whether infiltration has occurred essentially by evaluating the fluid flow rates through the IV tube during fluid withdrawal and infusion. For instance, if there is no infiltration, the time for withdrawal and the time for infusion will be substantially equal. Further, the volume of fluid withdrawn will be substantially equal to the volume infused. For one method of evaluation, the micropocessor measures the time period for withdrawal of the predetermined volume of fluid and compares this time period to the infusion time period to determine whether the IV infusion tube is infiltrated into the patient's tissue. More specifically, the microprocessor can determine the ratio of the withdrawal time period to the infusion time period to determine whether infiltration has occurred. Further, the microprocessor can determine the difference between the time period to withdraw a volume of fluid and the time period required to infuse this same volume of fluid to determine whether infiltration has occurred. Additionally, the time to withdraw or infuse a predetermined volume of fluid can be compared with a known norm. As indicated above, any of these evaluations can be used to determine whether there is infiltration.

In an alternate embodiment, the microprocessor determines the fluid flow rates through the IV tube during fluid withdrawal and infusion by holding the withdrawal and infusion times constant and determining the volume of fluid withdrawn from and infused into the patient. Again, if there is no infiltration, the volume withdrawn and the volume infused within a set period of time should be substantially equal. More specifically, for this method the microprocessor first controls the rate of rotation of the rotor of the stepper motor in the reverse mode to withdraw fluid from the patient at a preselected withdrawal pressure during a predetermined withdrawal period. To determine the volume of fluid withdrawn, the microprocessor measures the number of "steps" through which the rotor of the stepper motor rotates during the withdrawal period. The microprocessor then correlates the measured number of steps to a withdrawn volume of fluid.

In accordance with this alternate embodiment, the microprocessor next causes the rotor of the stepper motor to rotate in the forward mode to infuse fluid into the patient at a preselected infusion pressure during a predetermined infusion time period. The microprocessor measures the number of steps of the stepper motor during this infusion period, correlates the number to an infusion volume of fluid, and then compares the withdrawn volume of fluid to the infused volume of fluid to determine whether infiltration has occurred.

In yet another alternate embodiment, the microprocessor controls the stepper motor to alternately withdraw and infuse fluid at a preselected fluid flow rate. During withdrawal and infusion of the fluid at the preselected flow rate, the pressure transducer measures the pressure at which fluid is withdrawn and infused and sends a pressure signal to the microprocessor during fluid withdrawal and infusion. The microprocessor compares the fluid withdrawal pressure to the fluid infusion pressure to determine whether infiltration has occurred.

The novel features of this invention, as well as the invention itself, both as to its structure and its operation, will be best understood from the accompanying drawing, taken in conjunction with the accompanying description, in which similar reference characters refer to similar parts, and in which:

BRIEF DESCRIPTION OF THE DRAWINGS

FIG. 3 is a graph of the operating pressure of the novel IV infusion monitoring system versus time for one complete monitoring cycle;

FIG. 4 is a block diagram of the procedure for monitoring an IV infusion process in accordance with the present invention;

DESCRIPTION OF THE PREFERRED EMBODIMENT

Figure 1:
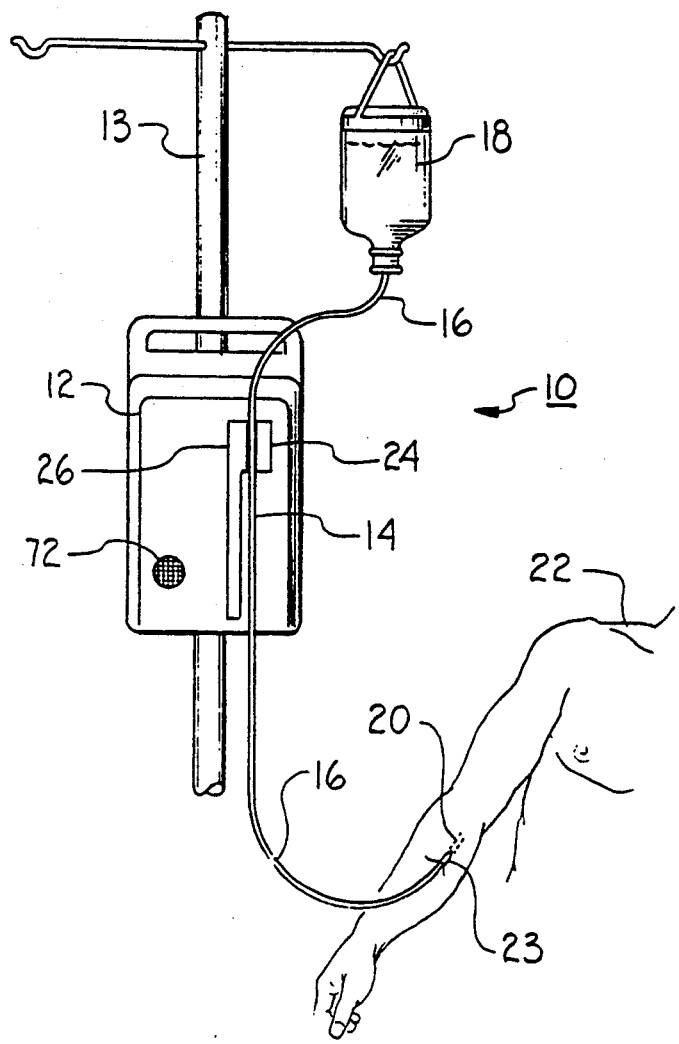
FIG. 1 is a perspective view of the novel IV infusion monitoring system of the present invention, seen in its intended environment with portions shown in phantom for clarity.

Referring initially to FIG. 1, a system, generally designated 10, is shown for monitoring an IV infusion procedure to determine whether an IV infusion set is undesirably infiltrated into a patient's tissue. More particularly, system 10 is shown to include a base 12 for holding a portion 14 of a resilient IV tube 16. Base 12 can be attached to an IV pole 13. As shown, IV tube 16 is connected in fluid communication to a fluid source 18 that contains the fluid to be infused into a vein 20 of patient 22. To establish fluid communication between tube 16 and patient 22, tube 16 is attached to a hollow needle 23 which is insertable into vein 20.

FIG. 1 also shows that a fluid pressure generator such as pump 24 having a platen 26 are mounted on base 12. As shown, portion 14 of IV tube 16 is positioned between the pumping mechanism of pump 24 and platen 26. In accordance with the present invention, pump 24 is a positive displacement pumping mechanism. Preferably, pump 24 is a peristaltic pump of the type marketed by IMED Corporation under the trade names "PC-1" and "PC-2". Pump 24 can, however, be any suitable rotary or linear peristaltic pump which pumps fluid through IV tube 16 by squeezing resilient portion 14 against platen 26 to create a moving zone of occlusion along portion 14. Indeed, pump 24 can be any suitable mechanism for generating pressure in IV tube 16 to urge fluid through tube 16.

Figure 2:
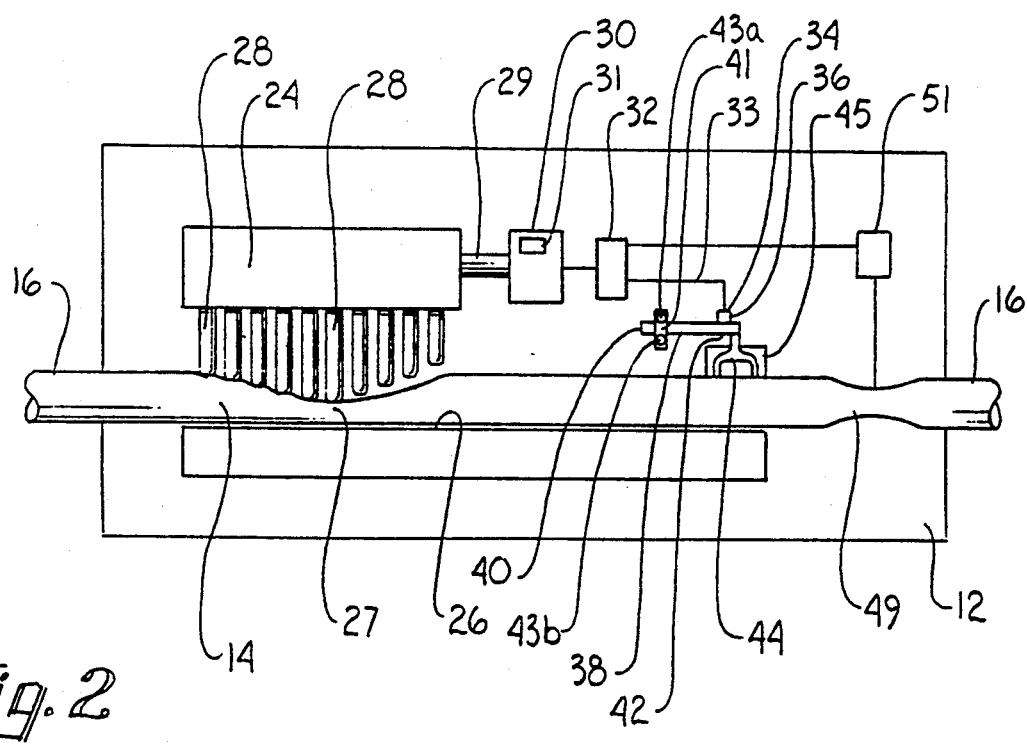
FIG. 2 is a schematic diagram of the operative components of the novel IV infusion monitoring system of the present invention.

FIG. 2 shows that peristaltic pump 24 preferably has a plurality of fingers 28 which sequentially occlude tube portion 14 to create a moving zone of occlusion 27. While FIG. 2 shows twelve fingers 28, it is to be understood that pump 24 can have more or less fingers for occluding portion 14 to pump fluid through IV tube 16. Additionally, FIG. 2 shows that pump 24 is mechanically coupled via a shaft 29 to a motor 30. In the preferred embodiment, motor 30 is a stepper motor that can be energized from a suitable dc power source, such as a battery (not shown). Each increment of rotation of the rotor (not shown) of stepper motor 30 causes the fingers 28 of pump 24 to urge in a concerted sequence against tube portion 14 to pump fluid through tube portion 14. More specifically, the rotor of motor 30 can rotate in a forward mode to cause fingers 28 of pump 24 to sequentially urge against tube portion 14 to infuse fluid from source 18 into patient 22 (shown in FIG. 1). Also, the rotor of motor 30 can rotate in a reverse mode to cause fingers 28 of pump 24 to urge against tube portion 14 to withdraw fluid from patient 22.

It is to be understood that the rate at which the rotor of motor 30 turns establishes the rate at which the fingers 28 of pump 24 sequentially squeeze tube portion 14. The rate at which fingers 28 squeeze tube portion 24 in turn establishes the fluid pressure within tube 16 downstream of pump 24. Consequently, the rate at which the rotor of motor 30 turns establishes the fluid pressure within tube 16 downstream of pump 24. Also, each increment of rotation of the rotor of stepper motor 30 corresponds to an incremental volume of fluid being pumped through IV tube 16 by pump 24.

As further shown in FIG. 2, a microprocessor 32, which includes a timer 31, is mounted on base 12, and motor 30 is electrically connected to microprocessor 32. In turn, microprocessor 32 is electrically connected via line 33 to a pressure transducer 34. Pressure transducer 34 is mounted on base 12 in operative engagement with IV tube 16 for the purpose of measuring the fluid pressure within IV tube 16 and generating an electrical signal representative of this pressure.

In accordance with the present invention, pressure transducer 34 can be a suitable pressure sensor. For example, pressure transducer 34 can be a bellows-type sensor. Preferably, however, pressure transducer 34 is a type of pressure sensor which does not require an entry site directly into IV tube 16 in order to measure the fluid pressure inside IV tube 16. Stated differently, transducer 34 can preferably measure fluid pressure inside IV tube 16 without requiring direct contact between transducer 34 and the fluid within IV tube 16.

In the preferred embodiment shown in FIG. 2, transducer 34 incorporates a strain gage 36, which may be piezoelectric, that is mounted on a strain beam 38. End 40 of strain beam 38 is held against base 12 by connecting flange 41. In turn, flange 41 is fixedly attached to base 12 by connectors 43a,b. End 42 of strain beam 38 is fixedly connected to a pressure sensing arm 44. Pressure sensing arm 44 is reciprocally mounted on base 12 and is positioned on base 12 in contact with IV tube 16. In accordance with the present invention, pressure sensing arm 44 can reciprocate in response to fluid pressure changes within resilient IV tube 16 within a channel 45 that is formed on base 12. It will be appreciated in reference to FIG. 2 that as arm 44 reciprocates, arm 44 causes strain beam 38 to deflect. Strain gage 36 senses these deflections in strain beam 38 and generates an electrical signal that is representative of the deflection of beam 38 (and, hence, fluid pressure within tube 16). The electrical signal from strain gage 36 is sent to microprocessor 32 via line 33. Finally, FIG. 2 shows that a suitable fluid flow sensor, e.g., a venturi 49, can be installed in portion 14 of IV tube 16 for sensing fluid flow rate through venturi 49. Venturi 49 is in turn connected to signal generator 51, which generates an electrical signal indicative of fluid flow through venturi 49. As shown in FIG. 2, signal generator 51 and sends this pressure signal to microprocessor 32.

OPERATION

During an infiltration check by system 10, microprocessor 32 causes pump 24 to alternately withdraw and infuse fluid from patient 22. During fluid withdrawal and infusion, microprocessor 32 causes system 10 to hold selected components of fluid flow through IV tube 16 constant while measuring other selected components of fluid flow to determine whether infiltration of the IV administration set has occurred. More specifically, system 10 holds selected components of fluid flow rate and fluid pressure within IV line 16 constant during fluid withdrawal and infusion, and measures other variable components of fluid flow rate and pressure through IV line 16 to determine whether infiltration has occurred.

In the preferred operation of system 10, needle 23 is inserted into patient 22. Then, for its normal operation, pump 24 is activated to infuse fluid from source 18 into patient 22. During the infusion process, however, system 10 periodically determines whether needle 23 is in fluid communication with vein 20 or is undesirably infiltrated into the tissue of patient 22 which surrounds vein 20.

In the preferred method for determining whether infiltration has occurred, fluid pressure within IV line 16 is varied while the total volume of fluid withdrawn and infused during the infiltration check is evaluated for constancy during fluid withdrawal and infusion. System 10 measures the time required for withdrawing the predetermined volume of fluid from patient 22 and the time required for infusing the predetermined volume of fluid into patient 22. System 10 then compares these times to each other or to a known norm to determine whether IV set infiltration has occurred.

More particularly, FIG. 3 shows that at a time $T_0$ the static fluid pressure of the patient 22 is used to establish a datum pressure $P_1$, i.e, motor 30 of pump 24 is momentarily stopped to obtain the fluid pressure in tube 16 downstream of pump 30 and establish this as a datum pressure having a value of $P_1$. At time $T_1$ in FIG. 2, system 10 commences an infiltration monitoring cycle. More specifically, as shown in cross-reference to FIGS. 1 and 2 and as indicated at block 48 in FIG. 4, microprocessor 32 sends a signal to stepper motor 30 to cause the rotor of stepper motor 30 to incrementally rotate in the reverse mode. Consequently, the pressure in tube 16 downstream of pump 24 decreases.

As indicated in FIG. 4, the pressure signal from transducer 34 is sent via line 33 to microprocessor 32. This enables microprocessor 32 to monitor the pressure within tube 16. As indicated in block 50, in response to the signal from transducer 34, microprocessor 32 controls the speed of rotation of stepper motor 30 to establish a preselected withdrawal pressure of $P_1$ minus a differential pressure ($\Delta P$) within tube 16 downstream of pump 24. In the preferred embodiment, $\Delta P$ is approximately equal to one half pounds per square inch (0.5 psi).

Furthermore, as indicated at block 52 of FIG. 3, microprocessor controls motor 30 of pump 24 to withdraw a predetermined volume of fluid through IV tube 16 from patient 22. To do this, microprocessor 32 correlates the predetermined volume to a number of incremental operational steps of motor 30. Stated differently, the predetermined volume is correlated by microprocessor 32 to a number of rotational increments of the rotor of motor 30, and microprocessor 32 causes the rotor of motor 30 to turn through the correlated number of increments. Thus, microprocessor 32 controls the speed of rotation of the rotor of motor 30 to establish the preselected withdrawal pressure. Additionally, microprocessor 32 controls the total number of operational increments of motor 30 to establish the predetermined volume of fluid to be withdrawn. In the preferred embodiment, the predetermined volume of fluid to be withdrawn is approximately fifteen microliters (15 $\mu$l).

FIG. 2 indicates that at time $T_3$, the rotor of motor 34 has rotated through the predetermined number of rotational increments, i.e., at time $T_3$, the predetermined volume of fluid has been withdrawn from patient 22. As indicated at block 54 in FIG. 4, timer 31 of microprocessor 32 measures the time of withdrawal ($T_3-T_2$) of the predetermined volume. Also at time $T_3$, microprocessor 32 causes motor 30 to operate in the forward mode to raise the pressure in tube 16 and infuse fluid into patient 22, as indicated at block 56 in FIG. 4. As recognized by the present invention, however, the period $T_3-T_2$ may be relatively long in the event that needle 23 is infiltrated into the tissue of patient 22. Thus, microprocessor 32 can cease operating motor 30 in a reverse mode and immediately alarm after a predetermined time period after time $T_2$.

As indicated at block 58, microprocessor 32 controls the speed of rotation of the rotor of motor 30 to establish a preselected infusion pressure within tube 16 of $P_1+\Delta P$.

At time $T_4$, pressure within tube 16 has reached $P_1+\Delta P$. Beginning at time $T_4$, microprocessor 32 causes the rotor of motor 30 to continue to turn in the forward mode through a predetermined number of rotational increments that is correlated to a predetermined volume of fluid to be infused into patient 22, as indicated at block 60. In accordance with the present invention, this predetermined volume of fluid to be infused is the same amount as the predetermined volume of fluid that was withdrawn from patient 22. Accordingly, microprocessor 34 controls the rate of rotation of the rotor of motor 34 and the total number of operational steps through which the rotor of motor 34 rotates to infuse the predetermined volume of fluid into patient 22 at the preselected infusion pressure.

At time $T_5$, the rotor of motor 34 has turned in the forward mode through the predetermined number of rotational increments. Thus, at time $T_5$, the predetermined volume of fluid has been infused into patient 22, and timer 31 of microprocessor 32 measures the time for infusion of the predetermined volume, as indicated at block 62. It will be appreciated that the time for infusion of the predetermined volume is equal to $T_5-T_4$.

As indicated at block 64, microprocessor 32 determines the ratio of the withdrawal time ($T_3-T_2$) to the infusion time ($T_5-T_4$). Additionally, microprocessor 32 determines the difference between the infusion time and the withdrawal time, as indicated at block 66. Based upon the determinations made by microprocessor 32 at blocks 64 and 66, microprocessor 32 determines whether the needle 23 of the IV administration set of the present invention is infiltrated into the tissue of patient 22, as indicated at block 68. More particularly, as recognized by the present invention, the ratio of the infusion time to the withdrawal time will be approximately equal to unity, and the difference between the infusion time and the withdrawal time will be approximately equal to zero when needle 23 is in fluid communication with vein 20. On the other hand, when needle 23 is infiltrated into the tissue surrounding vein 20, the ratio of the infusion time to the withdrawal time will be less than unity, and the absolute value of the difference between the infusion time and the withdrawal time will be greater than zero.

As indicated at block 70, in the event that microprocessor 32 determines that the IV administration set has become infiltrated into the tissue of patient 22, microprocessor 32 can activate an audio or visual advisory alarm 72, shown in FIG. 1 to indicate the status of the IV site. Also, as implied above, the withdrawal time or the infusion time can be evaluated in comparison with a preselected norm or value.

At time $T_5$, microprocessor 32 causes motor 30 to resume infusing fluid into patient 22 at the datum pressure $P_1$. System 10 is thus configured for another infiltration monitoring cycle at time $T_6$, or at some time period after $T_6$, e.g., system 10 could conduct an infiltration determination cycle as described above at fifteen minute intervals. It is to be understood that the interval between cycles can be established to be longer or shorter than fifteen minutes, as desired, by appropriately programming microprocessor 32. Importantly, the infiltration determination cycle can be performed immediately after the IV set has been established and before the actual infusion process is begun.

Figure 5:
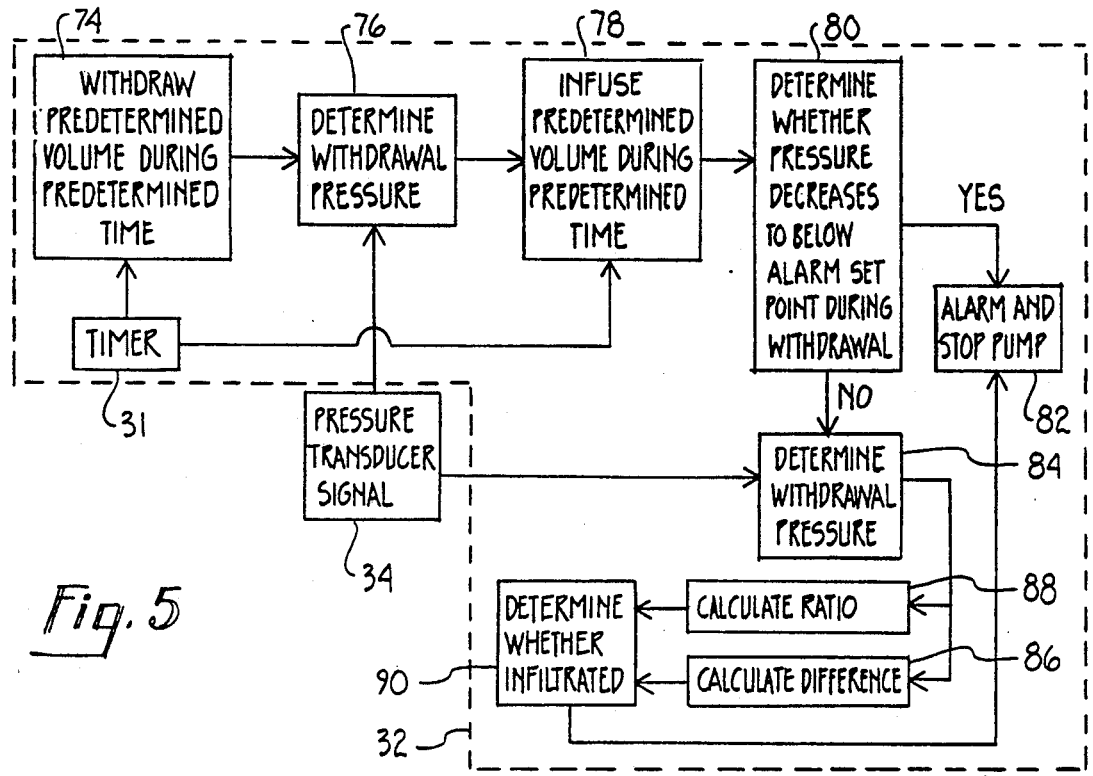
FIG. 5 is a block diagram of an alternate procedure for monitoring an IV infusion process.

An alternate method for determining whether an IV administration set is infiltrated into the tissue of a patient is represented in FIG. 5. As indicated at block 74 of FIG. 5, microprocessor 32 causes pump 24 to withdraw a predetermined volume of fluid from patient 22 during a predetermined time. To do this, microprocessor 32 correlates the predetermined volume to a number of operational steps of stepper motor 30, and then causes the rotor of stepper motor 30 to rotate in the reverse mode through the correlated number of operational steps during the predetermined withdrawal period, as measured by timer 31.

As fluid is being withdrawn from patient 22, pressure transducer 34 measures the fluid pressure within IV line 16 downstream of pump 24 and sends a signal representative of this pressure to microprocessor 32, as indicated at block 76. After the predetermined volume of fluid has been withdrawn, microprocessor 32 causes stepper motor 30 to rotate in the forward mode to infuse a predetermined volume of fluid into patient 22 during a predetermined infusion time period, as indicated at block 78.

As indicated at block 80, during the withdrawal time period microprocessor 32 monitors fluid pressure in IV line 16 downstream of pump 24. This fluid pressure is measured by pressure transducer 34 and sent to microprocessor 32 to enable microprocessor 32 to determine whether pressure in line 16 has decreased to below a preselected value. It will be appreciated that in the event infiltration has occurred, pressure in line 16 could decrease dramatically and potentially cause the collapse of line 16 before the predetermined volume of fluid has been withdrawn from patient 22. As indicated at block 82, if pressure in IV line 16 has decreased below the preselected value, microprocessor 32 activates alarm 72 to indicate an infiltration condition and deenergizes pump 24.

On the other hand, if pressure in line 16 remains above the preselected value, microprocessor 32 controls pump 24 to completely withdraw the predetermined volume of fluid from patient 22. As indicated at block 84, microprocessor 32 determines the pressure, as indicated by transducer 34 at which the predetermined volume of fluid was infused. Then, microprocessor 32 calculates the difference between and ratio of the withdrawal pressure to the infusion pressure, as respectively indicated at blocks 86, 88. Based upon either of the calculations at blocks 86 and 88, microprocessor 32 determines whether IV set infiltration has occurred, as indicated at block 90. If the IV set is indeed infiltrated, microprocessor activates alarm 72 and deenergizes pump 24, as indicated at block 82.

Figure 6:
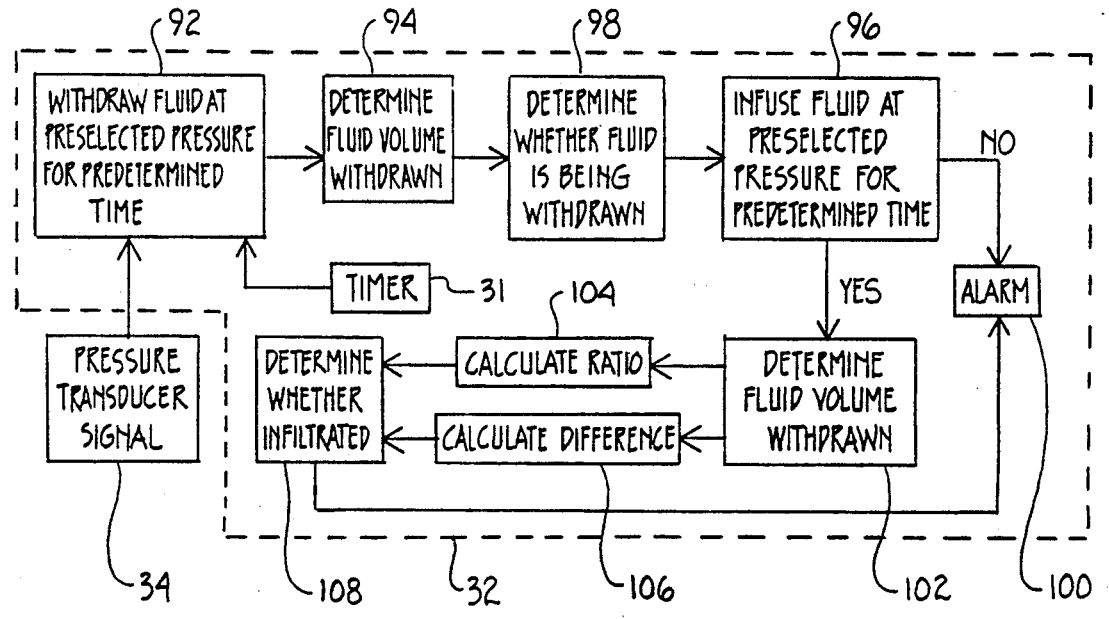
FIG. 6 is a block diagram of yet another alternate procedure for monitoring an IV infusion process.

FIG. 6 is a block diagram of yet another method by which microprocessor 32 can control system 10 to determine whether infiltration of the IV administration set has occurred. For this embodiment, as indicated at block 92, microprocessor 32 causes the rotor of stepper motor 30 to rotate in the reverse mode to cause pump 24 to withdraw fluid from patient 22. Microprocessor controls the speed of rotation of the rotor of stepper motor 30 to maintain a preselected pressure within IV line 16, as indicate pressure transducer 34. Microprocessor 32 continues to cause pump 24 to withdraw fluid into patient 22 for a predetermined time period, as measured by timer 31.

At the end of the predetermined time period, microprocessor 32 determines the volume of fluid which was withdrawn from patient 22, as indicated at block 94. To do this, microprocessor 32 counts the total number of steps through which the rotor of stepper motor 30 rotated, and correlates this number to a volume of fluid withdrawn. Alternatively, signal generator 51 can send a signal to microprocessor 32 which is representative of the fluid flow rate sensed by venturi 49. Microprocessor 32 can then correlate the fluid flow rate through venturi 49 to a total volume of fluid withdrawn by multiplying the fluid flow rate through venturi 49 by the predetermined withdrawal time period.

During the withdrawal step, it will be appreciated that in the event of IV set infiltration into the tissue of patient 22, pump 24 may have difficulty withdrawing fluid from patient 22, and that continued attempts to withdraw fluid may damage system 10 or patient 22. Accordingly, as indicated at block 98, microprocessor 32 determines whether fluid is being withdrawn from patient 22, either by monitoring whether the rotor of stepper motor 30 is rotating at an appropriate rate for withdrawing fluid, or by monitoring the fluid flow rate indication provided by venturi 49. In the event that fluid is not being satisfactorily withdrawn from patient 22, microprocessor 32 activates alarm 72 and deenergizes pump 24, as indicated at block 100.

Next, as indicated at block 96, microprocessor 32 causes the rotor of stepper motor 30 to operate in the forward mode to infuse fluid into patient 22 at a preselected pressure for a predetermined infusion time period. As indicated at block 102, microprocessor 32 determines the volume of fluid infused during the predetermined infusion time period. Microprocessor 32 then calculates the ratio of and difference between the volume of fluid infused and the volume of fluid withdrawn, as respectively indicated at blocks 104, 106. Based upon the calculations at blocks 104 or 106, microprocessor 32 determines whether IV set infiltration has occurred, as indicated at block 108. If the IV set is indeed infiltrated, microprocessor activates alarm 72 and deenergizes pump 24, as indicated at block 100.

While the particular IV administration set infiltration monitor as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

We claim:

1. An apparatus for determining abnormal fluid flow through an IV administration set, which comprises:
   an IV fluid tube connectable in fluid communication with the patient;
   a pump operatively engaged with said tube for causing fluid to flow through said tube;
   a pressure sensor operatively engaged with said tube between said pump and the patient for determining fluid pressure in said IV fluid tube;
   means electrically connected to said pressure sensor for operating said pump for withdrawing fluid having first flow characteristics from the patient and for operating said pump for infusing fluid having second flow characteristics to the patient, wherein said operating means causes said pump to withdraw a first volume of fluid from said vessel of the patient at a preselected withdrawal pressure during a first predetermined time interval, and said operating means causes said pump to infuse a second volume of fluid into said vessel of the patient at a preselected infusion pressure during a second predetermined time interval; and means for evaluating said first characteristics and said second characteristics to determine whether said IV administration set is infiltrated into the patient's tissue.

2. An apparatus as recited in claim 1 wherein said evaluating means compares said first time interval with said second time interval to determine whether said IV administration set is infiltrated.

3. An apparatus as recited in claim 2 wherein said preselected pressure for infusing fluid to the patient equals a datum pressure plus a differential pressure and said preselected pressure for withdrawing fluid from the patient equals said datum pressure minus said differential pressure.

4. An apparatus as recited in claim 3 wherein said differential pressure is approximately equal to one half pounds per square inch (0.5 psi).

5. An apparatus as recited in claim 2 wherein said predetermined volume of fluid is approximately equal to fifteen microliters (15 μl).

6. An apparatus as recited in claim 2 wherein said pump is a peristaltic pump for generating a moving zone of occlusion along said IV tube and said pressure sensor is located between said moving zone of occlusion and the patient during said first time interval and during said second time interval.

7. An apparatus as recited in claim 2 wherein said pump is operated in a reverse mode during said first time interval and is operated in a forward mode during said second time interval.

8. An apparatus as recited in claim 2 wherein said means for operating said pump is a stepper motor and said predetermined volume of fluid is correlated to a number of incremental steps of operation of said stepper motor.

9. An apparatus as recited in claim 2 further comprising means to alarm when said evaluating means compares said first time interval with said second time interval and determines that said IV administration set is infiltrated.

10. An apparatus as recited in claim 2 further comprising means to alarm when said evaluating means forms a ratio of said first time interval to said second time interval and exceeds a predetermined value.

11. An apparatus as recited in claim 1 wherein said evaluating means compares said first volume to said second volume to determine whether said IV administration set is infiltrated.

12. A method for determining whether there is abnormal fluid flow through an IV administration set, the set including a fluid source in fluid communication with a patient through an IV fluid tube and a pumping mechanism operatively engaged with the IV tube for pumping fluid through the IV tube, which comprises the steps of:

operating said pumping mechanism to withdraw fluid having withdrawal fluid flow characteristics from the patient, wherein said step of operating the pumping mechanism to withdraw fluid comprises withdrawing a first fluid volume of fluid from the patient at a preselected pressure during a predetermined time;

measuring selected components of said withdrawal fluid flow characteristics;

operating said pumping mechanism to infuse fluid having infusion fluid flow characteristics to the patient, wherein said step of operating said pumping mechanism to infuse fluid comprises infusing a second volume of fluid to the patient at a preselected pressure during a predetermined time interval;

measuring selected components of said infusion fluid flow characteristics; and comparing said selected components of said withdrawal fluid flow characteristics with said selected components of said infusion fluid flow characteristics for determining whether said IV administration set is experiencing abnormal fluid flow, wherein said step of comparing comprises comparing said first and said second volumes to determine whether there is abnormal fluid flow through said IV administration set.

13. An apparatus for determining abnormal fluid flow through an IV administration set, which comprises:

an IV fluid tube connectable in fluid communication with a patient;

a pump operatively engaged with said tube for causing fluid to flow through said tube;

a pressure sensor operatively engaged with said tube between said pump and the patient for determining fluid pressure in said IV fluid tube;

means electrically connected to said pressure sensor for operating said pump for withdrawing fluid having first flow characteristics from the patient and for operating said pump for infusing fluid having second flow characteristics to the patient, wherein said operating means causes said pump to infuse a predetermined volume of fluid to the patient during a predetermined time interval at an infusion pressure, and said operating means causes said pump to withdraw a predetermined volume of fluid from the patient during a predetermined time interval at a withdrawal pressure; and means for evaluating said first characteristics and said second characteristics to determine whether said IV administration set is infiltrated into the patient's tissue.

14. An apparatus as recited in claim 13 wherein said evaluating means compares said infusion pressure to said withdrawal pressure to determine whether said IV administration set is infiltrated.

15. A method for determining whether there is abnormal fluid flow through an IV administration set, the set including a fluid source in fluid communication with a patient through an IV fluid tube and a pumping mechanism operatively engaged with the IV tube for pumping fluid through the IV tube, which comprises the steps of:

operating said pumping mechanism to withdraw a predetermined volume of fluid from the patient at a first pressure during a predetermined time interval, and operating said pumping mechanism to infuse a predetermined volume of fluid to the patient at a second pressure during a predetermined time period, and comparing such first and second pressures to determine whether there is abnormal fluid flow through said IV administration set.

* * * * *